United States Patent
Zhou et al.

(10) Patent No.: US 6,962,749 B2
(45) Date of Patent: Nov. 8, 2005

(54) METHOD FOR IMPROVING STRENGTH OF ELASTIC STRAND

(75) Inventors: Peiguang Zhou, Appleton, WI (US); Wing-Chak Ng, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 323 days.

(21) Appl. No.: 10/313,059

(22) Filed: Dec. 5, 2002

(65) Prior Publication Data

US 2003/0094737 A1 May 22, 2003

Related U.S. Application Data

(62) Division of application No. 09/715,807, filed on Nov. 16, 2000, now Pat. No. 6,531,085.
(60) Provisional application No. 60/171,467, filed on Dec. 22, 1999, and provisional application No. 60/166,348, filed on Nov. 19, 1999.

(51) Int. Cl.[7] .............................. D01F 6/00; A61F 5/44

(52) U.S. Cl. ...................... 428/364; 428/370; 604/358
(58) Field of Search ................................ 428/364, 370; 604/358, 385.16

(56) References Cited

U.S. PATENT DOCUMENTS

| | | |
|---|---|---|
| 3,047,909 A | 8/1962 | Boyer |
| 3,644,157 A | 2/1972 | Draper |
| 3,692,618 A | 9/1972 | Dorschner et al. |
| 4,120,146 A | 10/1978 | Robin |
| 4,340,563 A | 7/1982 | Appel et al. |
| 4,940,464 A | 7/1990 | Van Gompel et al. |
| 5,187,917 A | 2/1993 | Mykleby |
| 5,428,076 A | 6/1995 | Roe |

(Continued)

FOREIGN PATENT DOCUMENTS

| | | |
|---|---|---|
| CA | 2260744 | 8/1999 |
| EP | 0 935 019 A1 | 8/1999 |
| JP | 07-309375 A | 11/1995 |
| WO | WO 97/49847 A1 | 12/1997 |
| WO | WO 01/36720 A1 | 5/2001 |
| WO | WO 01/36721 A1 | 5/2001 |
| WO | WO 01/36726 A1 | 5/2001 |

OTHER PUBLICATIONS

Billmeyer, Jr., Fred W., *Textbook of Polymer Science*, Second Edition, Wiley–Interscience, 1971, pp. 518–530.
Bird, R. Byron et al., *Transport Phenomena*, John Wiley & Sons, Inc., 1960, pp. 244–247.
McCabe, Warren L. and Julian C. Smith, *Unit Operations of Chemical Engineering*, Third Edition, McGraw–Hill Book Company, 1976, p. 748.
"Type S–7 Polyester Spandex Fiber Technology," Technical Information Bulletin, Globe Manufacturing Corp., 1999, pp. 1–24.

*Primary Examiner*—N. Edwards
(74) *Attorney, Agent, or Firm*—Patricia A. Charlier; Sebastian C. Pugliese III

(57) ABSTRACT

We have determined that strength characteristics of elastic strand improve when the strand is heated. Thus, the present invention is directed to improving strength characteristics of an elastic strand by heating the strand. The strand may be heated by thermal conduction and/or convection, by irradiative methods using, for example, infrared or microwave radiation, or some combination of these. If the elastic strand is made at a location different from the location where the strand is used as a raw material, the strand may be heated at either location, or both locations. Furthermore, the strand may be heated in-line, i.e. as part of the process that makes the strand or the process that uses the strand as a raw material, or off-line, i.e. in a step separate from either of the aforementioned processes. Finally, in addition to heat treating the strand, the strand's exposure to water or water vapor may be regulated to reduce or eliminate strength degradation.

20 Claims, 5 Drawing Sheets

U.S. PATENT DOCUMENTS

| | | |
|---|---|---|
| 5,536,921 A | 7/1996 | Hedrick et al. |
| 5,773,105 A | 6/1998 | Klett |
| 5,827,583 A | 10/1998 | Ambler |
| 5,885,524 A | 3/1999 | Watanabe et al. |
| 5,902,297 A | 5/1999 | Sauer |
| 5,904,672 A | 5/1999 | LeMahieu et al. |
| 5,904,675 A | 5/1999 | Laux et al. |
| 5,916,203 A | 6/1999 | Brandon et al. |
| 5,964,973 A | 10/1999 | Heath et al. |
| 6,143,947 A | 11/2000 | Noda |
| 6,176,371 B1 | 1/2001 | Tyrrell |
| 6,226,438 B1 | 5/2001 | Bylander et al. |
| 6,531,085 B1 | 3/2003 | Zhou et al. ............... 214/474 |
| 6,540,951 B1 * | 4/2003 | Zhou et al. ............... 264/340 |
| 6,582,413 B2 * | 6/2003 | Krautkramer et al. . 604/385.16 |
| 6,713,140 B2 * | 3/2004 | McCormack et al. ...... 428/36.6 |

* cited by examiner

METHOD FOR IMPROVING STRENGTH OF ELASTIC STRAND

This application is a division of Ser. No. 09/715,807 filed Nov. 16, 2000, now U.S. Pat. No. 6,531,085, which claims priority from U.S. Provisional Application Nos. 60/166,348 filed on Nov. 19, 1999 and 60/171,467 filed on Dec. 22, 1999.

BACKGROUND

People rely on disposable absorbent articles to help participate in, and enjoy, their daily activities.

Disposable absorbent articles, such as adult incontinence articles and diapers, are generally manufactured by combining several components. These components typically include a liquid-permeable topsheet; a liquid-impermeable backsheet attached to the topsheet; and an absorbent core located between the topsheet and the backsheet. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core is designed to have desirable physical properties, e.g. a high absorbent capacity and high absorption rate, so that bodily fluids can be transported from the skin of the wearer into the disposable absorbent article.

Some disposable absorbent articles are constructed with various types of elasticized waistbands and elasticized leg bands or leg cuffs. One method of constructing elasticized regions is to incorporate elastic strands into the disposable absorbent product. For example, elastic strands have been laminated between layers of polymer film and/or layers of woven or nonwoven fabrics to provide such regions. Folded-over layers have also been employed to enclose or envelop selected strands of material. These folded-over layers have been employed to enclose elastomeric strands within the waistband, leg cuff and inner barrier cuff components of disposable diapers and other disposable absorbent articles. The polymeric film or films, layers of woven or nonwoven fabrics, and/or folded-over layers may be an integral portion of the topsheet and/or backsheet discussed above, or may be separate components that are attached to the topsheet and/or backsheet.

In order to introduce an elastic strand to the product being made, a spool of the strand is generally placed on an unwind stand. The strand is then continuously unwound, in the machine direction, with the strand being attached to a substrate, such as a base layer of material, to provide a substrate composite. As stated above, examples of a base material include, but are not limited to, polymeric films and/or woven or nonwoven fabrics. If the elastic strand does not have the integrity to withstand forces placed on it during production of the article being made, then the strand may break. For example, the tension placed on a segment of the elastic strand between an unwind stand and the point of attachment on a base material may exceed the tensile strength of that segment, causing a break. Such breaks lead to costly downtime. Accordingly, producers of disposable absorbent articles, as well as other manufacturers using elastic strand as raw material in a production process, seek ways of ensuring that the strength characteristics of the elastic strand are sufficient to withstand forces placed on the elastic strand during production, thereby decreasing or minimizing the number of breaks. Furthermore, producers of articles, such as disposable absorbent articles, seek ways of improving the function of the elastic strand in the article. Typically, one function is to help define elasticized regions so that the disposable absorbent article better fits the wearer of the article. One way of decreasing the number of strand breaks on a production machine, improving the function of elastic strand in an article, or both, is to increase certain strength characteristics of elastic strand.

Accordingly, what is needed is a method for treating an elastic strand to improve the strength of the strand; and substrate composites or disposable absorbent articles comprising such strand.

SUMMARY

We have determined that strength characteristics of elastic strand improve when the strand is heated. Thus, the present invention is directed to improving strength characteristics of an elastic strand by heating the strand. The strand may be heated by thermal conduction and/or convection, or by irradiative methods, incorporating, for example, infrared radiation or microwave radiation, or some combination of these. If the elastic strand is made at a location different from the location where the strand is used as a raw material, the strand may be heated at either location, or both locations. Furthermore, the strand may be heated in-line, i.e. as part of the process that makes the strand or the process that uses the strand as a raw material, or off-line, i.e. in a step separate from either of the aforementioned processes. And, as noted below, the strand may be heat treated and its exposure to water or water vapor may be regulated.

One method having features of the present invention includes the steps of: providing an elastic strand, the elastic strand having been made by steps comprising extruding, spinning, or otherwise making the strand; and heating the strand so that the peak-load value of the heated elastic strand is about 10% greater, specifically about 20% greater, particularly about 30% greater, and more particularly about 40% greater than the peak-load value of the elastic strand before heating.

In some representative embodiments, the elastic strand comprises polyester, polyurethane, polyether, polyamide, polyacrylate, polyester-b-polyurethane block co-polymer, polyether-b-polyurethane block co-polymer, or polyether-b-polyamide block-co-polymer.

Methods by which the elastic strand may be heated include use of infrared radiation, microwave radiation, convective heat, conductive heat, or some combination thereof.

Some methods having features of the present invention include the steps of: providing an elastic strand, the elastic strand having been made by steps comprising extruding, spinning, or otherwise making the strand; and directing the strand to an environment having a temperature of about 120° F. or more, the strand remaining in the environment for about 4 or more hours, particularly about 8 or more hours, and more particularly about 24 or more hours.

Other methods having features of the present invention include the steps of: providing an elastic strand, the elastic strand having been made by steps comprising extruding, spinning, or otherwise making the strand; and directing the strand to an environment having a temperature of about 212° F. or more, the strand remaining in the environment for about 2 or more hours, particularly about 4 or more hours, and more particularly about 8 or more hours.

Still other methods having features of the present invention include the steps of: providing an elastic strand, the elastic strand having been made by steps comprising extruding, spinning, or otherwise making the strand; and directing the strand to an environment having a temperature of about 150° C. or more, the strand remaining in the environment for about 10 or more minutes, particularly about 20 or more minutes, and more particularly about 30 or more minutes.

In some representative embodiments, the strand is heated in-line on a production machine used to make a substrate composite comprising the strand or a disposable absorbent article comprising the strand.

In other embodiments of the present invention, the elastic strand is processed by steps comprising: providing an elastic strand, the elastic strand having been made by steps comprising extruding, spinning, or otherwise making the strand; heating the strand so that the peak-load value of the heated elastic strand is about 10% greater, specifically about 20% greater, particularly about 30% greater, and more particularly about 40% greater than the peak-load value of the elastic strand before heating; and regulating exposure of the strand to water or water vapor, as disclosed in co-pending U.S. patent application Ser. No. 60/166,348, entitled "Method for Regulating Strength Degradation in an Elastic Strand," which was filed on 19 Nov. 1999 and from which the present non-provisional application both claims priority and incorporates by reference in a manner consistent herewith. The co-pending application is generally directed to a method for regulating exposure of an elastic strand to water or water vapor, thereby regulating degradation of strength characteristics of the strand due to the action of water vapor or water on the strand. Accordingly, the present invention is directed to methods encompassing both heat treating the elastic strand to increase its strength characteristics, and regulating exposure of the strand to water or water vapor to minimize or eliminate strength degradation.

Examples of various methods for regulating elastic strand's exposure to water or water vapor which may be used before, during, or after heating of elastic strand given below.

In some embodiments, elastic strand's exposure to water vapor is regulated before, during, or after heating such that the specific humidity around the strand does not exceed about 0.01 pounds-mass of water vapor per pound-mass of dry air, specifically about 0.05 pounds-mass of water vapor per pound-mass of dry air during: production of the strand, storage of the strand at the geographic site where the elastic strand is made, shipping of the strand between the geographic site where the elastic strand is made and the geographic site where the elastic strand is to be used as a raw material, storage of the elastic strand at the geographic site where the elastic strand is to be used as a raw material, use of the elastic strand as a raw material, or some combination thereof. In one aspect, the elastic strand is used as a raw material to produce a substrate composite comprising the elastic strand or an absorbent article comprising the elastic strand.

In another aspect, the elastic strand's exposure to water vapor is regulated during shipping of the strand between the geographic site where the elastic strand is made and the geographic site where the elastic strand is used as a raw material.

In some representative embodiments, regulating the strand's exposure to water vapor comprises controlling the temperature around the strand or around a container that contains the strand. For example, the temperature may be controlled to a value not exceeding about 55 degrees Fahrenheit. By regulating temperature, the maximum humidity that may be attained is regulated (i.e., as air temperature decreases, the capacity of the air to hold water vapor decreases).

In other versions of the invention, wherein regulating the strand's exposure to water vapor comprises controlling the humidity around the strand or around a container that contains the strand.

In other versions of the invention, regulating the elastic strand's exposure to water vapor before or after heating of the strand comprises placing the strand in a container comprising a barrier material and closing the container.

In another aspect, the container comprising a barrier material is closed at a time $t_1$, time $t_1$ being after the time when the strand is first produced and before the time when the strand is shipped from the geographical site at which the strand is first produced to the geographical site at which the strand is used.

In still another aspect, the specific humidity around the strand does not exceed about 0.017 pounds-mass of water vapor per pound-mass of dry air, particularly about 0.01 pounds-mass of water vapor per pound-mass of dry air, and specifically about 0.005 pounds-mass of water vapor per pound-mass of dry air, between time $t_1$ and time $t_2$, time $t_2$ being the time when the closed container comprising a barrier material is first opened.

In some versions of the invention the barrier material comprises polyethylene, polypropylene, polyvinyl chloride, polyvinylidene chloride, polyester, polycarbonate, nylon, cellulose, or a combination thereof.

In another aspect, closing the container comprising a barrier material comprises heat sealing the container, the barrier material, or both.

Some representative embodiments involve placing desiccant material with the strand before heat sealing the container, the barrier material, or both. Possible desiccant materials comprise calcium chloride, calcium sulfate, silica gel, a molecular sieve, $Al_2O_3$, or some combination of thereof.

In other versions of the invention, any mixture of air and water vapor inside the container comprising a barrier material is displaced with an inert dry gas before heat sealing the container, the barrier material, or both; placing a humidity indicator inside the container comprising a barrier material before heat sealing the container, the barrier material, or both; or both of these steps.

The invention encompasses elastic strand that is heated to increase strength, as well as substrate composites and/or disposable absorbent products comprising said strand. Furthermore, as mentioned above, the elastic strand may also be handled such that the strand's exposure to water or water vapor is regulated before, during, or after heat treatment of the strand.

These and other features, aspects, and advantages of the present invention will become better understood with regard to the following description, appended claims, and accompanying drawings.

DRAWINGS

DESCRIPTION

The present invention is directed to improving strength in elastic strand by heating the strand. Increased strength provides an opportunity for improved performance of the strand and/or products or substrate composites incorporating the strand. Furthermore, increased strength may decrease, minimize, or eliminate strand breaks on a production machine using the elastic strand as a raw material (e.g., a conventional, high-speed, disposable-absorbent-article production process running at about 1000 feet per minute or more). Generally a method of the present invention involves heating the strand with heated air, or some form of radiation, such as microwave radiation or infrared radiation, or some combination of these. If the strand is made at a location different from the location where the strand is being used as a raw material, the elastic strand may be heated at the location where it is made, at the location where it is used as a raw material, or both. Furthermore, the strand may be heated in-line, i.e. as part of either the process for making the strand or the process in which the strand is used as a raw material, or off-line, i.e. as a step separate from either of these processes. One method having features of the present invention includes the steps of: providing an elastic strand, the elastic strand having been made by steps comprising extruding, spinning, or otherwise making the strand; and heating the elastic strand so that the peak-load value of the heated elastic strand is about 10% greater, specifically about 20% greater, particularly about 30% greater, and more particularly about 40% greater than the peak-load value of the elastic strand before heating. These and other embodiments are discussed in more detail in the following paragraphs.

Figure 1:
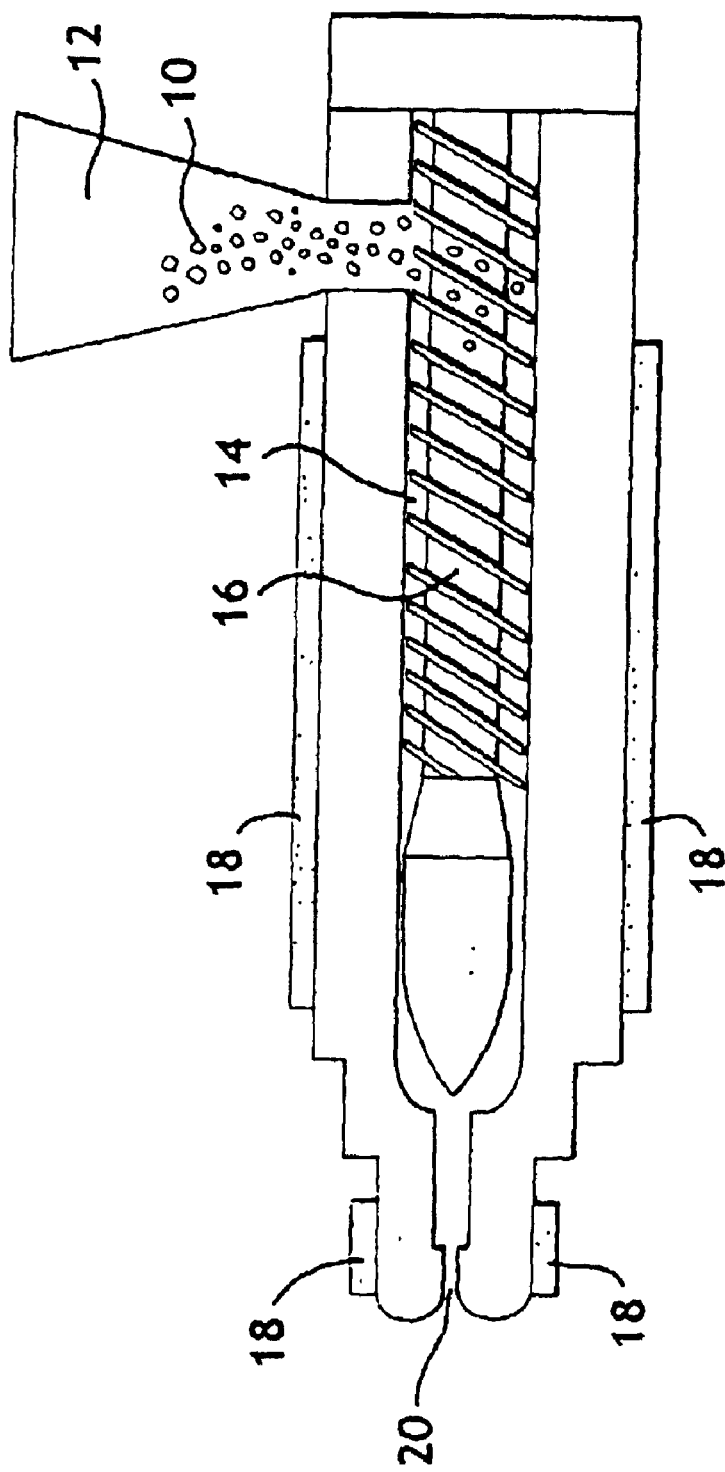
FIG. 1 shows a sectional view of one apparatus for making an elastic strand.

An elastic strand may be made in various ways, including, but not limited to extrusion and spinning. In an extrusion process, depicted in FIG. 1, polymer chips, particulates, pellets, or other solid forms 10 are placed in a hopper 12. The solid polymer is directed from the hopper to a chamber 14. The polymer is propelled continuously through the chamber by a rotating screw 16. As the polymer proceeds through the chamber, the temperature and pressure are such that the solid polymer melts and is compacted. Some of the heat is generated by friction, but typically, an external heating source 18 is also used to heat the polymer. The molten polymer is then forced through a die 20 to give a strand, continuous fiber, or filament of a desired structural shape. Possible cross-sectional shapes include, but are not limited to, circular, tri-lobal, polyhedral, rectangular (e.g., a ribbon-like structure), or ellipsoidal shapes. The strand cools and solidifies after exiting the extruder.

Rather than use a polymer as a feed material, one or more monomers may be added to the extruder in chip, particulate, pellet or other solid form. Alternatively, a pre-polymer having a molecular weight greater than that of the monomer, but less than that of the final polymer, may be added to the extruder. The monomers or pre-polymers may be added with compounds that promote polymerization. Polymerization occurs within the extruder chamber, but may or may not be complete before the material exits through the die. If polymerization is not complete, then some polymerization could occur after the material is extruded. Also, some of the monomer or pre-polymer may not ultimately react to become a part of a polymeric chain in the strand.

A number of materials may be extruded to give an elastic strand including, but not limited to: polyester; polyurethane; polyether; polyamide; polyacrylate; or combinations thereof, including random, block, or graft copolymers such as polyester-b-polyurethane block copolymers, polyether-b-polyurethane block copolymers, and/or polyether-b-polyamide block copolymers. As stated above, monomeric or pre-polymeric precursors may be added to the extruder to give the polymeric materials of the type just recited.

The present invention may be used in conjunction with the subject matter disclosed in co-pending U.S. patent application Ser. No. 60/166,348. When the elastic strand is susceptible to attack by water (e.g., by hydrolysis), then degradation of the strand's strength due to the action of water may be regulated by regulating the strand's exposure to water or water vapor. If the elastic strand is made, stored, shipped, or otherwise processed so that the strength of the strand degrades significantly due to the action of water or water vapor, then heat treatment of the strand in accordance with the present invention will likely be less effective in improving strength. As discussed below, the strand's exposure to water or water vapor may be regulated before the strand is heated, when the strand is heated, after the strand is heated, or some combination thereof.

Crosslinking agents may also be used when making an elastic strand. To the extent that polymeric chains are crosslinked, it is more likely that crosslinking reactions are initiated after the material is extruded. This may be accomplished, for example, in a separate processing step after the strand is extruded.

After the strand exits the extruder, it may be subjected to additional processing steps. These processing steps may take place at some location between extrusion of the strand and the strand being wound up at a bobbin, spindle, or spool for the first time. Alternatively, one or more of these processing steps may take place after the strand has been wound up for the first time. After a bobbin of elastic strand is made, it may later be unwound and treated in some fashion prior to its being wound up again.

Additional processing steps include, but are not limited to, the following. Air might be directed at the strand exiting the die to increase the cooling rate. A scouring step might be included to remove impurities from the strand by exposing the strand to soaps or detergents. A lubricant may be applied to the strand to reduce friction between strands or between the strand and pieces of equipment. Possible lubricants include, but are not limited to, a vegetable or mineral oil, a suitably refined petroleum product, a silicone-based material, or a surfactant. And a drawing step may be included to help orient the polymers to produce desirable physical properties. In one example of a separate drawing step, the strand is directed over two sets of rolls. The strand passes over a first set of rolls moving at a first velocity, then passes over a second set of rolls moving at a second velocity, the second velocity being greater than the first velocity. The difference in velocity between the first and second sets of rolls increases tension on the strand, thereby helping to orient the constituent polymers of the strand, change physical dimensions of the strand, or effect other changes.

After these or other additional processing steps, the strand is wound up for storage or shipment to another geographic location. During this or other steps in which a spool, reel, or bobbin of an elastic strand is unwound and then wound, the strand may be treated with various additives such as cleaning agents, lubricants, or dyes.

In addition to the example of an extrusion process discussed above, various spinning processes may be used to produce an elastic strand or fiber. In general, these processes require dissolving the polymer in solution or melting the polymer.

Figure 2:
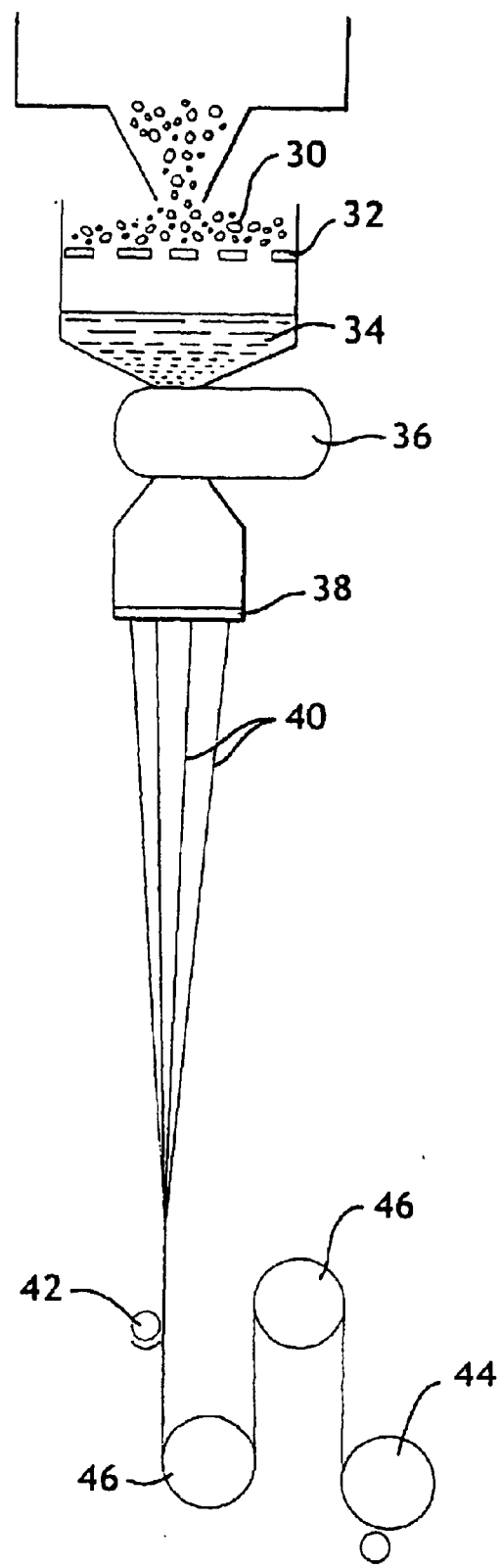
FIG. 2 shows a sectional view of one apparatus for making an elastic strand.

In a melt spinning process, as depicted in FIG. 2, polymer chips, particulates, pellets, or other solid forms 30 are heated by a heated-metal grid 32 or other heating device. The resulting molten polymer 34 is pumped under high pressure through a plate called a spinneret 38. The plate generally defines a plurality of small holes. The molten polymer emerges from the face of the spinneret, usually into air, and solidifies. A number of these strands 40 may be brought together to form a cable- or rope-like structure comprising a plurality of strands.

The polymer typically is melted by contacting a hot grid in the form of steel tubing, which is heated electrically, or by some other means. A metering pump 36, or a combination of a metering pump and a booster pump, may be used to conduct the molten polymer to, and through, the spinneret. Alternatively, an extrusion-type screw may be used to help melt the polymer, and meter the resulting molten polymer, to and through the spinneret.

Generally strands or filaments emerge from the spinneret face into air and begin to cool. Air jets or blasts directed at the emerging strands may be used to speed up the cooling process. After the strands or filaments have traveled far enough to solidify they are processed further. As stated above, additional process steps include, but are not limited to, scouring, lubricating, or drawing the strand or strands. FIG. 2, for example, depicts a lubricating disk and trough 42 for applying a lubricant to one or more strands. After processing is complete the strand—in this case a cable- or rope-like structure—is wound up on a reel, spindle, spool, or bobbin 44 at a winding station. Before being wound up, the strand may pass over one or more rolls 46.

Other spinning processes include wet spinning, in which a solution of a polymer or polymer derivative emerges from a spinneret into a liquid that coagulates the polymer or polymer derivative to form a strand; and dry spinning in which a solution of polymer emerges from the spinneret into air or an inert gas atmosphere into which solvent evaporates, thereby forming a filament or strand. Examples of such methods are given in FRED W. BILLMEYER, JR., TEXTBOOK OF POLYMER SCIENCE, pp. 518–530 (Wiley-Interscience, 2d ed. 1971).

Generally, the same polymeric, pre-polymeric, or monomeric materials useful for extruding an elastic strand are also useful for spinning an elastic strand. Examples of such materials are discussed above. Also, crosslinking agents may be used. Again crosslinking will likely be effected after the strand or filament emerges from the spinneret.

It should be understood that the above discussion gives exemplars of ways of making elastic strand. The present invention is not limited to these exemplars, but may be used in conjunction with other processes that make an elastic strand whose strength properties may be improved by heating.

Before referring to data demonstrating that heating an elastic strand improves the strand's strength, it is advantageous to discuss certain terms. As discussed herein, "peak load" or "peak-load value" refers to the tensile load placed on a strand, measured in grams, when the strand breaks or fails. Furthermore, "tensile strength," peak load, and peak-load value are used synonymously in this specification. But it should be understood that other measures might be used to characterize the effect of heating on an elastic strand's strength or integrity. As discussed herein, "elongation" refers to the change in length per unit length at peak load. Typically, elongation is recited as a percentage.

Figure 3:
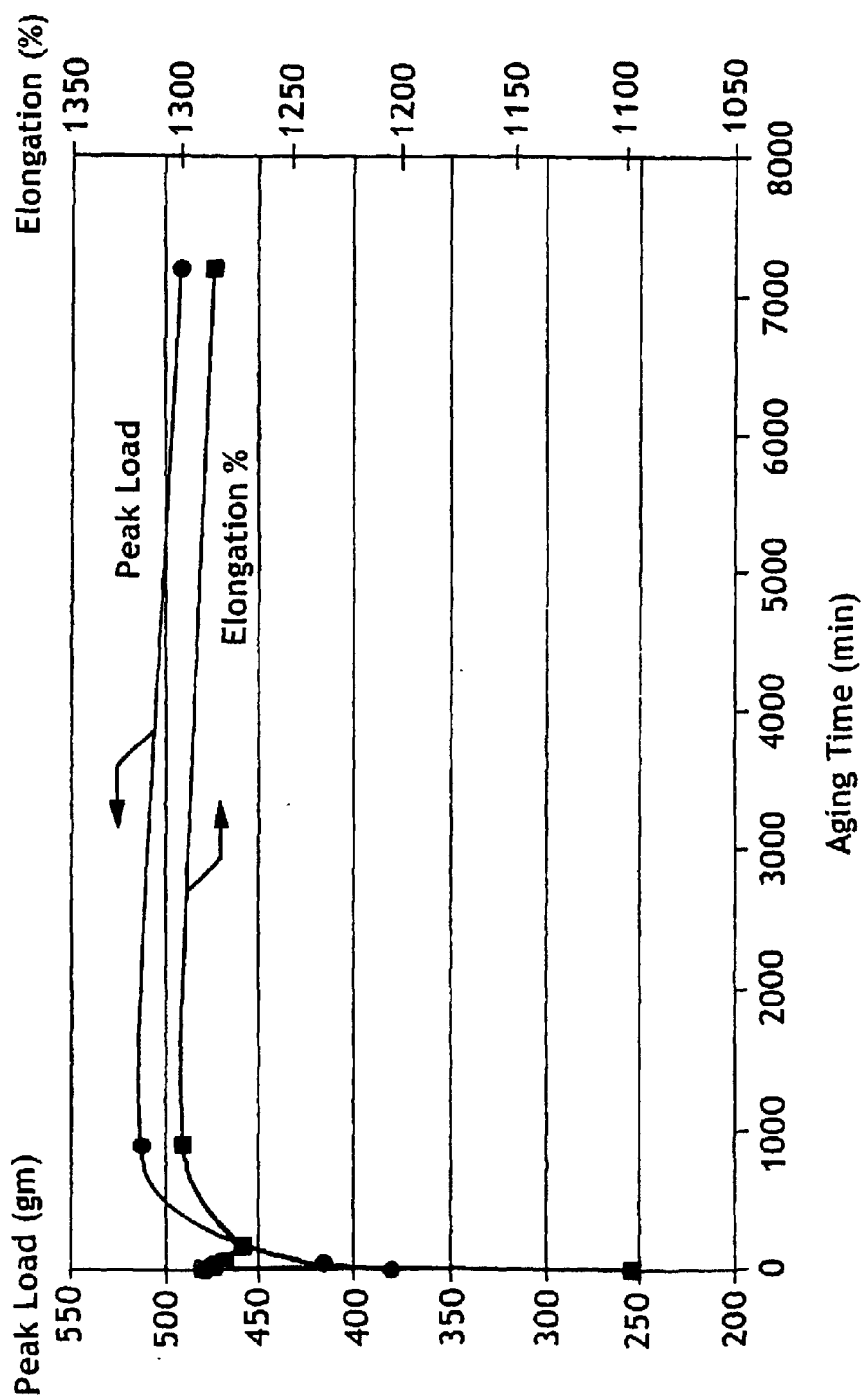
FIG. 3 shows a plot of peak-load value, in grams, and percent elongation as a function of time of exposure to a specified temperature.

FIG. 3 (discussed below under Examples) shows that exposure to a temperature of 212° F. increased the peak-load value of an elastic strand sold under the trademark GLOSPAN 840, a material made by Globe Manufacturing Company, a business having offices at Fall River, Mass. GLOSPAN 840 comprises a polyester-b-polyurethane block copolymer. After a sample of the strand was placed in a forced-air oven at the recited temperature for approximately two hours, the peak-load value increased from approximately 375 grams to about 460 grams, an increase of more than 20%. After the strand was exposed to this same temperature for 1000 minutes in the forced-air oven, the peak-load value increased from approximately 375 grams to about 510 grams, an increase of more than 35%.

The preceding example shows that the strength properties of elastic strand may be improved by heating. As stated above, elastic strand may be heated by hot air—i.e., by thermal conduction and/or convective heat transport, or by an irradiative method incorporating, for example, microwave radiation or infrared radiation, or by some combination thereof. If the elastic strand, or bobbins of elastic strand, are heated in a separate process step (i.e., off-line), then the strand or bobbins may be heated, for example, in a forced-air oven, in a microwave oven, or under infrared lamps. If, on the other hand, the strand is heated as part of a process for making the strand or using the strand as a raw material (i.e., in-line), then microwave radiation, infrared radiation, hot air, or some combination of these may be directed at the moving strand to heat the strand.

If an oven is the only device used to heat the strand, then the strand will typically be heated in a step separate from a process used to make the strand, or a process that uses the elastic strand as a raw material. As shown in FIG. 3, the time required to improve the strength characteristics of the strand are such that an oven alone would generally not be placed in-line with equipment used to make the strand, or equipment used to incorporate the strand into a composite or product. While the oven temperature could be increased above 100° C. to increase the rate at which the strand is heated, the temperature cannot be raised so high that the polymeric constituents of the strand degrade. It should be noted, however, that a method relying on convection and conduction to heat the strand, e.g. directing hot air at the strand, could be combined with one or more irradiative methods to heat the strand in-line (discussed below).

To heat the elastic strand in a step separate from a strand production process or a process that uses the strand as a raw material (i.e., off-line), spools, bobbins, or reels of the strand may be placed in an oven at a selected temperature and for a selected time. Alternatively, heated air at a selected temperature may be directed at the spools, bobbins, or reels for a selected time. As demonstrated in the Examples below, simple experiments may be carried out to determine the improvement in strength of a particular elastic strand material at specific temperatures. Furthermore, analytical techniques may be used to ascertain whether an elastic strand material degrades at specified temperatures. From this combination of data—i.e., strength-versus-time curves for an elastic-strand material at a given temperature and analytical results showing whether or not the polymeric constituents of the strand degrade at that temperature—a treatment temperature and time may be selected that gives the desired increase in strength.

For example, FIG. 3 shows that the peak-load value of GLOSPAN 840 increased from approximately 375 grams to about 460 grams, an increase of more than 20%, after this elastic strand material was placed in a forced-air oven at a temperature of 100° C. for approximately two hours. Additional work (described below under Examples) demonstrated that the peak-load value of GLOSPAN 840 could be increased by about 20% after being exposed to a temperature of 150° C. for 15 minutes. But the peak-load value of GLOSPAN 840 decreased by 30% when this elastic strand material was placed in a forced-air oven at a temperature of 216° C. for 5 minutes. Furthermore, thermogravimetric analysis indicated that the polymeric constituents of GLOSPAN 840 begin decomposing at a temperature of about 240° C. (with temperature being increased at a rate of 10° C. per minute). This latter information shows that the temperature can be increased to increase the rate of heating and the rate of strength improvement—but only to a point. Above a certain temperature the strength of the elastic strand material is degraded, not improved, likely because the polymeric constituents of the strand begin to degrade or decompose.

Based on the preceding information, a manufacturer or user of GLOSPAN 840 could place this elastic strand material in a forced-air oven at a temperature of 150° C. for 15 minutes to boost strength about 20%. Note, however, that a manufacturer or user of GLOSPAN 840 is likely to put an entire spool of the strand in the oven, not just a single sample of the strand as discussed in the example above. Some spools of strand have a plastic core with a 3-inch radius and a 10-inch length, with the strand wound around the core so that the strand material extends radially outwardly from the outer surface of the plastic core approximately 3 inches. Other spool geometries are possible. Basic heat transfer principles, such as those discussed in R. BYRON BIRD ET AL., TRANSPORT PHENOMENA (John Wiley & Sons 1960) (with a discussion of Fourier's law of heat conduction at pp. 244–47), suggest that it will take longer for heat to be conducted through, for example, a 3-inch layer of strand material on a spool compared to the time required to conduct heat throughout a single strand. Examples 7 and 8 below appear to demonstrate that this is the case for GLOSPAN 1060. After 4 hours of treatment at 100° C., the peak-load value of individual strands was about 640 grams (Example 7), while the peak-load value of samples taken from a bobbin averaged about 605 grams (with the value of 605 grams corresponding to the average of 592 grams, 614 grams, and 608 grams measure after a 4-hour treatment time; see Example 8). Accordingly, the time required to boost the strength of elastic strand on a spool or bobbin would likely take longer than the experimental results for individual strands suggest.

Spools or bobbins of the strand may be placed in an oven either at the location where the elastic strand is made or at the location where the elastic strand is used as a raw material (if the location where the strand is used is different from the location where the strand is produced). For example, bobbins of elastic strand, after the strand is first wound up at the site where the strand is made, could be placed in a forced-air oven at a temperature of 100° C. or more for 2 or more hours. Alternatively, the strand could be placed in a forced-air oven at a temperature of 150° C. or more, possibly for a shorter period of time. After the strand was heat treated, the bobbins could be prepared for shipment, or could be stored for some period of time prior to shipment.

Other approaches can be used to heat the strand. For example, an infrared light could be placed in close proximity to an elastic strand in order to irradiate the strand. One example of an infrared light is a 250W infrared lamp available form TechniLab Instruments, Inc., of Requannock, N.J. Absorption of infrared radiation by the polymeric constituents of the strand would generate heat, thereby heating the strand. Furthermore, an infrared light, or a plurality of lights, can be located in close proximity to the strand after it has been extruded or spun, but before it is wound up on a bobbin for the first time (i.e., in-line at the site where the elastic strand is made). If there is a separate processing step in which a bobbin is unwound, treated, and then wound up again, then an infrared light, or plurality of infrared lights, could be used to heat-treat the strand during a separate processing step.

Alternatively, the elastic strand can be irradiated with microwave radiation to heat the strand. A suitable microwave generator and cavity is described in U.S. Pat. No. 5,536,921, issued Jul. 16, 1996 to Hedrick et al., which is hereby incorporated by reference in a manner consistent herewith. This device, useful for on-line treatment of sheet-like materials, may also be used for in-line treatment of elastic strand. The device comprises a cylindrical single-mode model TM010 resonating-cavity microwave applicator, and is available from International Business Machines Corporation, a business having offices at Armonk, N.Y. The diameter of the applicator of this model is 4 inches, and the output power can be adjusted continuously up to 6.0 kW at a frequency of 2450 MHz. The elastic strand can be directed through the cavity so that the strand is exposed to a plurality of microwave standing waves within the cavity. As the elastic material passes through the standing waves the incident microwave energy is converted into heat within the strand. An example of using a microwave generator to continuously treat a web, rather than a strand, is given in U.S. Pat. No. 5,916,203 issued 29 Jun. 1999 to Brandon et al. and entitled "Composite Material with Elasticized Portions and a Method of Making the Same," which is hereby incorporated by reference in a manner consistent herewith. This same approach can be used to heat an elastic strand, or a plurality of elastic strands.

One or more of the above-identified methods may be used in combination to heat an elastic strand, or plurality of elastic strands. For example, an infrared light, or several infrared lights, could be used in combination with streams of hot air directed at a strand to heat the strand. Or streams of hot air could be directed at the strand before or after the strand was exposed to microwave radiation in a cavity as discussed above. Any combination of ways in which energy is transmitted to the elastic strand so that the strand is heated, thereby improving the strength of the strand, is encompassed by the present invention. So, for example, the strand could be heated by hot air, infrared radiation from infrared lamps, and microwave radiation as discussed above.

As discussed in co-pending U.S. Patent Application No. 60/166,348, in some instances bobbins of elastic strand, after being first wound up, may be processed or treated in some fashion by unwinding the bobbin, treating the strand, and then winding the strand up once more. This co-pending application also discloses that an elastic strand's exposure to water vapor can be regulated in order to regulate strength degradation in the strand. Thus an elastic strand that is heat treated by the manufacturer of the strand can also be processed, stored, handled, or shipped in a manner that regulates exposure of the strand to water vapor.

Co-pending U.S. Patent Application No. 60/166,348 gives a number of examples by which an elastic strand's exposure to water vapor can be regulated. These same methods may be used with elastic strand before it is heat treated, after it is heat treated, or both before and after the strand is heat treated. If the elastic strand has already been heat treated, then bobbins, spools, or reels of the heat-treated strand may be stored in a controlled-humidity or controlled-temperature room or facility. If these bobbins are shipped to another location, then these bobbins can be packaged in a container comprising a barrier material resistant to the penetration of water vapor. If the elastic strand is placed in a container comprising a barrier material while in a low-humidity environment, then the micro-environment immediately around the elastic strand inside the container will correspond to that low-humidity environment. After the container is closed (e.g. by thermally sealing a plastic bag), subsequent processing steps can be carried out so that the humidity or temperature outside the container is not regulated. In one aspect, the container would likely not be opened until the elastic strand was to be used as a raw material in a production process.

As disclosed in co-pending U.S. patent application No. 60/166,348, a desiccant material may be placed near the elastic strand—including elastic strand that has been heat treated—before closing the container comprising a barrier material. To the extent that the container allows water vapor to penetrate into and around the elastic strand, the desiccant acts to preferentially adsorb or absorb the water vapor. Accordingly, the desiccant helps to keep the humidity inside the container at a level that minimizes strength degradation.

In another aspect, a humidity detector or indicator is placed with the elastic strand—again the elastic strand may already have been heat-treated—before the container comprising a barrier material is closed. When the bag or container is opened, most likely after it has been shipped to a purchaser of the elastic strand, the humidity detector can be examined to determine if the humidity inside the container exceeded a certain value. If the humidity did exceed a certain value, then the bag or container could be rejected and sent back to the supplier. Alternatively, a sample from the shipment could be tested immediately. If the strength characteristics of the strand were deemed acceptable, then the shipment could be accepted for use as a raw material.

Rather than heat the strand at the site where the strand is made, bobbins of the elastic strand can be heated at the site where the strand is used as a raw material. If the elastic strand is not shipped in a sealed container comprising a barrier material, then the elastic strand could be heated when it is received, or after storage but prior to the strand being used as a raw material. If the elastic strand is stored prior to use, the strand could be stored in an environment in which humidity is regulated, either by controlling humidity directly or by controlling temperature, as disclosed in co-pending U.S. Patent Application No. 60/166,348.

If the elastic strand were shipped in a container comprising a barrier material, then the elastic strand would likely not be heated until the container is opened. Thus, for example, the containers of elastic strand could be stored for a period of time prior to the containers being opened. After the container is opened and bobbins of the elastic strand are removed, the bobbins could be placed in an oven for a selected temperature and time to obtain a desired increase in a strength characteristic (e.g., peak-load value). Alternatively, the bobbins may be placed in a microwave oven to obtain the desired increase in strength. Rather than heat treat the strand off-line, the elastic strand could be irradiated with microwave radiation or infrared radiation, and/or impinged with hot air at some location between the unwind stand and the strand's point of attachment on a base material to make a substrate composite (i.e., in-line). In each case, readily available or acquired data may be used to select the heat-treatment conditions necessary to achieve a given strength improvement.

Additional Detail on Regulating Strength Degradation in Elastic Strand

As discussed above, methods for improving strength of elastic strand may be combined with methods for regulating strength degradation in elastic strand by regulating the strand's exposure to water or water vapor. Before proceeding to a more detailed discussion of some representative ways in which a strand's exposure to water or water vapor may be regulated, it is useful to review certain additional definitions. The term specific humidity generally refers to the mass of vapor carried by a unit mass of vapor-free gas. As used herein, "specific humidity" refers to the mass of water vapor carried by a unit mass of vapor-free gas, the gas typically being air. The term relative humidity generally refers to the ratio of the partial pressure of the vapor to the vapor pressure of the liquid at the gas temperature. It is usually expressed on a percentage basis, so 100 percent relative humidity means that the gas is saturated with vapor and 0 percent relative humidity means that the gas is vapor free. As used herein, "relative humidity" refers to the ratio of the partial pressure of water vapor to the vapor pressure of water at the gas temperature, the gas typically being air. For purposes of this document, "humidity" refers to a measure of the amount of water vapor in a gas, typically air, and unless stated otherwise, refers to specific humidity and/or relative humidity. The term dew point generally refers to the temperature at which a vapor-gas mixture must be cooled—at constant humidity—to become saturated. As used herein, "dew point" refers to the temperature at which a water vapor-gas mixture must be cooled—at constant humidity—to become saturated, the gas generally being air.

One way in which a strand's exposure to water vapor may be regulated is to conduct one or more of the processing and/or handling steps following extrusion or spinning in a controlled-humidity environment. This is generally accomplished by carrying out one or more of said steps in a room, compartment, or other enclosure in which a value corresponding to the humidity in the enclosure is controlled so that it does not exceed a selected set point. The set point corresponds to a desired specific humidity or relative humidity. Control generally comprises first sensing or measuring a value corresponding to the specific humidity or relative humidity in the enclosure. Typically, the device used to sense or measure humidity will be in the vicinity of the elastic strand. The sensed or measured value is transmitted to a controller, computer, or other device that compares the sensed or measured value to a set-point value. If the sensed or measured value is sufficiently different from the set-point value, then a control action is taken such that the specific humidity or relative humidity in the enclosure is force adjusted to be at or below the desired specific humidity or relative humidity.

Typically, the specific humidity or relative humidity is force adjusted by directing the air/water-vapor mixture across cooling coils so that the temperature of the mixture is reduced below the mixture's dew point. As a result of this cooling process, a portion of the water vapor condenses on the coils and is removed as liquid, thereby reducing humidity. By directing a sufficient amount of the air/water-vapor mixture across the cooling coils, and then conducting the dehumidified air into the enclosure, humidity is force adjusted to the desired level. After water vapor has been condensed and removed by this cooling process, the air may be heated to increase the dry-bulb temperature. As used herein, "dry-bulb temperature" refers to the temperature of the air/water-vapor mixture as indicated by a thermometer placed in the mixture. Accordingly, as used herein, "controlled-humidity" refers to environments in which specific humidity and/or relative humidity are controlled, and, if the air is heated to increase the dry-bulb temperature after the air/water vapor mixture is dehumidified, environments in which the dry-bulb temperature is also controlled or regulated.

The air/water vapor mixture may be taken from inside the enclosure, dehumidified, and then recirculated back to the enclosure; or it may be taken from outside the enclosure, dehumidified, and brought into the enclosure; or both. For example, if an enclosure is built around a winding station to which an elastic strand is continuously directed, there will be an opening in the enclosure to allow the strand to enter and be wound up. If the manufacturing environment is hot and humid, then a slight positive pressure will likely be maintained inside the enclosure to reduce the amount of hot, humid air entering the enclosure through the opening. In this case, some quantity of the air/water vapor mixture outside the enclosure will have to be dehumidified and brought into the enclosure to replace the air/water vapor mixture inside the enclosure that is escaping through the opening because of the positive pressure.

Rather than control humidity so that it is at or below a set-point value, the air inside the room or enclosure can be cooled to a temperature set point such that the maximum specific humidity cannot exceed a certain level. Humidity charts for air at atmospheric pressure may be used to select the appropriate temperature set point. For example, at a temperature of 40° F., even at a relative humidity of 100%, the specific humidity is about 0.006 $lb_m$ of water vapor per $lb_m$ of dry air. This value is less than ¼ of the specific humidity that resulted in a 60% drop in peak-load value over a 60 day period (see Example 10 below). Accordingly, as used herein, "controlled-temperature" refers to environments in which temperature is controlled to some value in order to regulate the amount of water vapor experienced by the elastic strand.

As stated above, one embodiment of the invention is directed to controlling the humidity of one or more of the processing and/or handling steps following extrusion or spinning. Alternatively, the temperature of the processing and/or handling step(s) may be controlled to limit the capacity of the air to hold water vapor. For example, the step in which the elastic strand is first wound up at a winder may be carried out in a controlled-humidity or controlled-temperature environment. Processing steps upstream or downstream of the first winder may also be carried out in a controlled-humidity or controlled-temperature environment. As used herein, "first winder" refers to the winder at which the strand is first wound up after it is extruded or spun; "upstream" refers to those processing steps that occur after the strand is extruded or spun, but before the first winder; and "downstream" refers to those processing steps that occur after the first winder. If one or more additional processing steps occur after the first winding step at a separate unwinding/winding station (i.e., a station where the elastic strand is unwound, processed in some way, and rewound), these one or more additional processing steps may be carried out in a controlled-humidity or controlled-temperature environment. To the extent that bobbins of elastic strand are stored prior to use or shipment, the bobbins may be stored in a controlled-humidity or controlled-temperature environment. If elastic strand is being shipped to another location, the step in which the elastic strand is prepared—perhaps involving another step in which the elastic strand is unwound and then wound back up again—and packaged for shipment may also be carried out in a controlled-humidity or controlled-temperature environment. And the step of shipping or transporting the elastic strand itself may be carried out in a controlled-humidity or controlled-temperature environment.

All of these steps—winding, storing, preparing and packaging for shipment (if shipping is necessary), shipping, and perhaps storing again at the location where the strand will be used as a raw material—can be carried out in a controlled-humidity or controlled-temperature environment such that the tensile strength of the strand at the time it is used as a raw material on a production machine has not decreased by more than about 20%, particularly about 10%, and specifically about 5% from the tensile strength of the strand at the time it was first produced or prepared for shipment.

In some cases, however, not all of the steps need be carried out in a controlled-humidity or controlled-temperature environment. For example, the elastic strand can be placed in a container comprising a barrier material. As used herein, "barrier material" refers to a material that is resistant to penetration by water vapor. The step of placing elastic strand in a container comprising a barrier material, i.e. packaging the elastic strand for storage or shipment, may be accomplished in a number of ways. Bobbins of elastic strand, or pallets of bobbins of elastic strand, can be wrapped or encased by a barrier material, e.g. a suitable shrink-wrap. Alternatively, bobbins of elastic strand, or pallets of bobbins of elastic strand, may be placed in a flexible plastic bag comprising a barrier material. Or the elastic strand may be placed in a box or carton comprising a barrier material, e.g. lined with or holding a flexible plastic bag that is resistant to penetration by water vapor. Other types of containers comprising a barrier material may be used.

If the elastic strand is placed in a container comprising a barrier material while in a low-humidity environment, then the micro-environment immediately around the elastic strand inside the container will correspond to that low-humidity environment. Subsequent processing steps might be carried out such that the humidity or temperature outside the container is not regulated. The container would likely not be opened until the elastic strand was to be used as a raw material in a production process.

A number of methods may be used to package the elastic strand. The elastic strand may be wound up at a first winder in a controlled-humidity or controlled-temperature environment, and then taken, conducted, or conveyed to a controlled-humidity or controlled-temperature environment for packaging. Alternatively, the elastic strand may be wound up at a first winder and, soon thereafter, taken, conducted, or conveyed to a controlled-humidity or controlled-temperature environment for packaging.

While in a controlled-humidity or controlled-temperature environment, bobbins of elastic strand, or pallets of bobbins of elastic strand are placed in a container comprising a barrier material. Suitable barrier materials that are resistant to penetration by water vapor include, but are not limited to, polyethylene, polypropylene, some of the other materials discussed above, or a combination thereof. The container is then closed in a way that minimizes the amount of water vapor that might reach the packaged strand during subsequent storage and/or shipping steps. For example, if the container comprising a barrier material is a flexible polyethylene bag or other flexible, water-vapor-resistant plastic bag, then the container can be heat sealed after bobbins of elastic strand, or pallets of bobbins of elastic strand, are inserted into the bag. Alternatively, bobbins of elastic strand, or pallets of bobbins of elastic strand, can be placed in a carton or box lined with a barrier material such as a polyethylene bag, the bag being heat sealed after the bobbins of elastic strand are in place.

Desiccant material may be placed near the elastic strand prior to the container comprising a barrier material being closed, e.g. heat sealed. To the extent that the container allows water vapor to penetrate into and around the elastic strand, the desiccant acts to preferentially adsorb or absorb the water vapor. Accordingly, the desiccant helps to keep the humidity inside the container at a level that minimizes strength degradation.

Examples of useful desiccants include calcium chloride, calcium sulfate, silica gel, some of the other materials discussed above, and the like. Typically, the desiccant will be put in a receptacle that allows passage of water vapor into the interior of the receptacle and in contact with the desiccant, but keeps the desiccant separate from the elastic strand. An example of a receptacle is a pouch comprising a fibrous web of naturally-occurring fibers—typically having cellulose as a primary constituent—or a nonwoven material such as a polyethylene or polypropylene nonwoven fabric that that is made to allow passage of water vapor.

In another aspect, the present invention further comprises the step of displacing the air/water vapor mixture inside the container comprising a barrier material with a dry, inert gas before closing the container. For example, after pallets of bobbins of elastic strand have been placed inside a container, dry nitrogen gas may be directed to the interior of the container using a flexible conduit. After sufficient time has passed to allow displacement of the air/water-vapor mixture from inside the container, the conduit is removed from the container, and the container is then closed. This displacement step may be used in conjunction with the step of placing a desiccant material with the elastic strand prior to closing the container. In an alternative method, the packaging system may be configured so that any air/water-vapor mixture inside the container comprising a barrier material is evacuated prior to the container being closed.

In another aspect, a humidity detector is placed with the elastic strand before the container comprising a barrier material is closed. When the bag or container is opened, most likely after it has been shipped to a purchaser of the elastic strand, the humidity detector can be examined to determine if the humidity inside the container exceeded a certain value. If the humidity did exceed a certain value, then the bag or container could be rejected and sent back to the supplier. Alternatively, a sample from the shipment could be tested immediately. If the strength characteristics of the strand were deemed acceptable, then the shipment could be accepted for use as a raw material. One example of a suitable humidity detector is the humidity indicator corresponding to catalogue number HC-10/60-200, available from Omega Engineering Inc., of Stamford, Conn. The indicator is capable of detecting relative humidity over the range 10 to 60 percent.

The step of placing a humidity detector with the elastic strand may be used in conjunction with: placing a desiccant with the strand before a container comprising a barrier material is closed; displacing the air/water-vapor mixture inside the container comprising a barrier material with a dry, inert gas before closing the container; or both.

In some embodiments of the present invention, bobbins of elastic strand are stored either at the site where the strand is made, at the site where the strand is used as a raw material, or both. If the strand is not packaged during these storage steps, and the strand is to be stored for more than 10, specifically more than 20, and particularly more than 30 days, then the room, facility, or area in which the strand is stored may be a controlled-humidity or controlled-temperature environment if the ambient humidity is such that the strand's strength might be significantly degraded. But, as discussed above, all of the process and handling steps subsequent to the strand being extruded or spun may be carried out in controlled-humidity or controlled-temperature environment—regardless of the total time between extrusion or spinning of the strand and use of the strand as a raw material—to minimize or eliminate strength degradation. Or the elastic strand can be packaged so that the "microenvironment" inside the container comprising a barrier material has a low water-vapor content (i.e., a low humidity), thereby allowing subsequent processing steps to be carried out such that the environment outside the package need not be controlled.

Elastic strands processed or handled in accordance with the present invention may be incorporated into a number of substrate composites and disposable absorbent articles. Examples of such substrate composites and/or disposable absorbent articles are described in U.S. Pat. No. 4,940,464, entitled "Disposable Incontinence Garment or Training Pant," which is hereby incorporated by reference in a manner consistent with the present specification; U.S. Pat. No. 5,904,675, entitled "Absorbent Article with Improved Elastic Margins and Containment System," which is hereby incorporated by reference in a manner consistent herewith, with column 7, lines 7 through 34 discussing use of elastic strands with a containment flap, and column 9, line 29 through column 10, line 36 discussing elastic members; U.S. Pat. No. 5,904,672, entitled "Absorbent Article having Improved Waist Region Dryness and Method of Manufacture," which is hereby incorporated by reference in a manner consistent with the present specification, with column 11, line 39 through column 12, line 2 discussing elastic leg members; and U.S. Pat. No. 5,902,297, entitled "Absorbent Article Having a Collection Conduit," which is hereby incorporated by reference in a manner consistent herewith, with column 4, lines 18 through 48 discussing elasticized leg and waist members. It should be understood that the present invention is applicable to other structures, composites, or products incorporating one or more elastic strands that are heat-treated to improve strength, whose exposure to water or water vapor has been regulated to regulate strength degradation, or both.

An example of a method and apparatus for making an elastomeric laminate web (i.e., for purposes of the present application, a substrate composite incorporating elastic strand) which may be used with the present invention is found in U.S. Pat. No. 5,964,973, entitled "Method and Apparatus for Making an Elastomeric Laminate Web," which is hereby incorporated by reference in a manner consistent with the present specification. Again it should be understood that this patent gives exemplars of methods and apparatuses for incorporating elastic strands into substrate composites, and the present invention may be used with other methods and apparatuses used to make substrate composites.

EXAMPLES

Example 1

A bobbin of GLOSPAN 840 (Globe), an elastic strand comprising a polyester-b-polyurethane block copolymer, was obtained from Globe Manufacturing Company. The elastic strand had been coated with a silicone-based lubricant. Samples of the strand were placed in a forced-air oven, model number OV490A-2, made by Blue M, a business having offices at Blum Island, Ill. The oven was preheated to a temperature of 100° C. prior to samples of the strand being placed in the oven. At selected times of exposure to these conditions, samples of the strand were withdrawn from the oven and taken to a testing room. Generally about 15 to 30 minutes elapsed between the time the sample was withdrawn from the controlled environment and the time the sample was tested.

Figure 4:
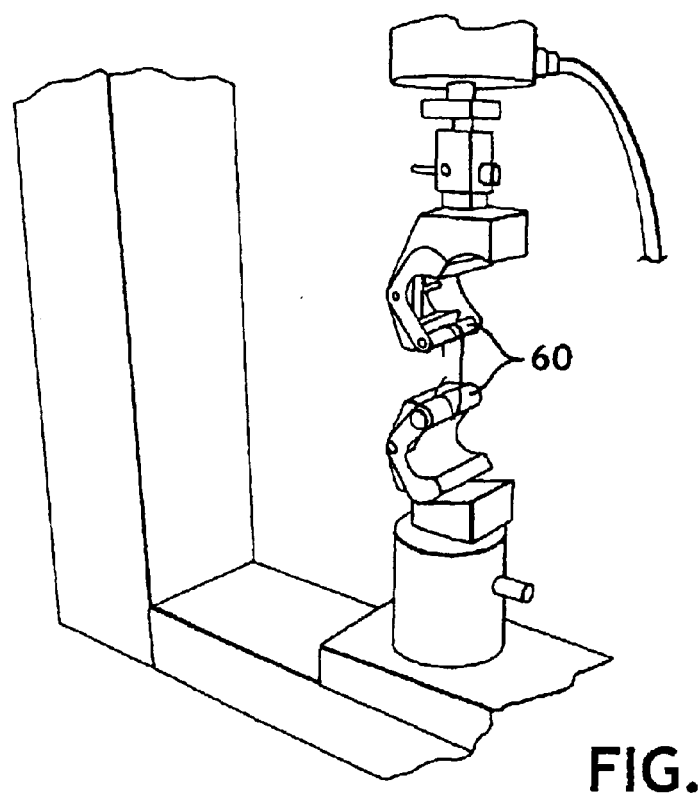
FIGS. 4 and 4A show perspective views of a tensile tester.
Figure 4A:
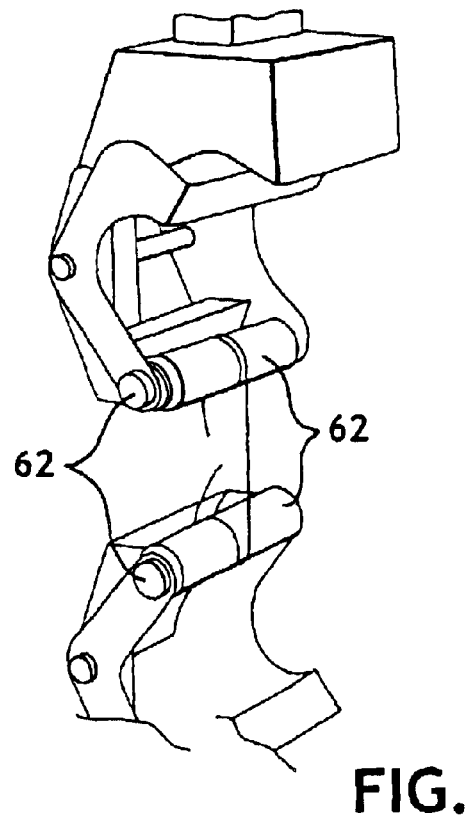

Both the tensile strength and the elongation of a strand sample were determined using a Sintech tensile tester, available from MTS System Corporation, a business having offices at Eden Prairie, Minn. The opposing holders on the tensile tester consisted of cylindrical rods 60, as shown in FIGS. 4 and 4.A. The gauge length was set at 1.5 inches by moving the holders such that the central axes 62 of the rods were 1.5 inches apart. One end of a length of strand was then wrapped twice around one cylinder. The other end was then taken and wrapped twice around the other cylinder. The tester was activated so that the opposing holders moved in opposite directions at a crosshead speed of 20±0.4 inches $\text{min}^{-1}$. The strand was pulled apart at this speed until the strand broke. The peak-load value, in grams, and percent elongation, which reflects the change in length per unit length, were recorded at the point where the strand broke. Values plotted in FIG. 3 reflect the average of 5–10 replicates. This testing process was repeated at selected times of exposure to the specified temperature to give the plot depicted in FIG. 3.

Example 2

The forced-air oven described in Example 1 was preheated to a temperature of 150° C. A sample of GLOSPAN 840, taken from the same bobbin discussed in Example 1, was placed in the oven at this recited temperature. After 15 minutes, the strand was removed and tested using the procedure outlined in Example 1. The peak-load value was found to increase from about 375 grams to about 450 grams, or about a 20% increase, due to heating the strand at this time and temperature.

Example 3

The forced-air oven described in Example 1 was preheated to a temperature of 216° C. A sample of GLOSPAN 840, taken from the same bobbin discussed in Example 1, was placed in the oven at this recited temperature. After 5 minutes, the strand was removed and tested using the procedure outlined in Example 1. The peak-load value was found to decrease from about 375 grams to about 265 grams, or about a 30% decrease, due to heating the strand at this time and temperature.

Example 4

The thermal stability of a sample of GLOSPAN 840 was determined using thermogravimetric analysis and differential scanning calorimetry. For the thermogravimetric analysis, a sample of GLOSPAN 840 was placed in a sample holder in the heating element of a Model 951 Thermogravimetric Analyzer made by TA Instruments, a business having offices in New Castle, Del. The sample was heated from room temperature, which was approximately 21° C., to a temperature of 450° C. at a heating rate of 10° C. per minute. The sample was heated under a dynamic atmosphere of air with an airflow of approximately 80 milliliters per minute. The crucible was continuously weighed during heating so that any decrease in weight could be detected. The resulting weight-change curve, i.e. a plot of sample weight versus temperature, showed that GLOSPAN 840 had a decomposition temperature of about 240° C. in air.

For the analysis using differential scanning calorimetry, a 10 milligram sample of GLOSPAN 840 was placed in the sample chamber of the heating/cooling block of a Model 2920 differential scanning calorimetry analyzer made by TA Instruments. The sample was heated from −100° C. to 200° C., then cooled to −100° C., then reheated again to 200° C., at a heating and cooling rate of 10° C. per minute. A Liquid Nitrogen Cooling Accessory, also made by TA Instruments, was attached to the Model 2920 differential scanning calorimeter. The results indicated that there were no significant peaks showing energy absorption or evolution over the temperature range from about 20° C. to about 200° C. Thus GLOSPAN 840 appears to be oxidatively and thermally stable over this range of temperatures.

Example 5

An 8-inch long sample from the bobbin of GLOSPAN 840 (discussed in Example 1 above) was placed under a 250-watt infrared lamp available from TechniLab Instruments, Inc., a business having offices in Requannock, N.J. The distance between the strand and the surface of the lamp was 1.5 inches. After 30 seconds, the strand was removed from its position under the lamp and tested using the procedure outlined in Example 1 above. The peak-load value of the strand increased from about 375 grams to about 410 grams, or about a 10% increase in strength.

Example 6

A strand from a bobbin of GLOSPAN 840 discussed in Example 1 above was continuously directed through a cavity so that the strand was exposed to a plurality of microwave standing waves inside the cavity. The microwave generator and cavity that was used is generally described in U.S. Pat. No. 5,536,921, issued Jul. 16, 1996 to Hedrick et al. As discussed above under the Description section, this document is incorporated by reference in a manner consistent with the present application. The device comprises a cylindrical single-mode resonating-cavity microwave applicator, designated as model number TM101, which is available from International Business Machines Corporation, a business having offices in Armonk, N.Y. The diameter of the applicator of this model is 4 inches, and the output power can be adjusted continuously up to 6.0 kW at a frequency of 2450 MHz. With the power adjusted to 2.0 kilowatts, the strand was directed through the cavity at a speed of about 50 feet per minute. Under these conditions, the strand was exposed to microwave energy for about 1–2 seconds. The peak-load value of the irradiated strand was determined using the procedure outlined in Example 1 above. The peak-load value of strand treated in this manner increased from about 375 grams to about 410 grams, or about a 10% increase in strength.

Example 7

A bobbin of GLOSPAN 1060, an elastic strand comprising a polyester-b-polyurethane block copolymer, was obtained from Globe Manufacturing Company. The elastic strand had been coated with a silicone-based lubricant. Samples of the strand were placed in a forced-air oven, model number OV-490A-2, made by Blue M, a business having offices at Blum Island, Ill. The oven was preheated to a temperature of 100° C. prior to samples of the strand being placed in the oven. At selected times of exposure to these conditions, samples of the strand were withdrawn from the oven and taken to a testing room. Generally about 15 to 30 minutes elapsed between the time a sample was withdrawn from the controlled environment and the time the sample was tested.

Figure 5:
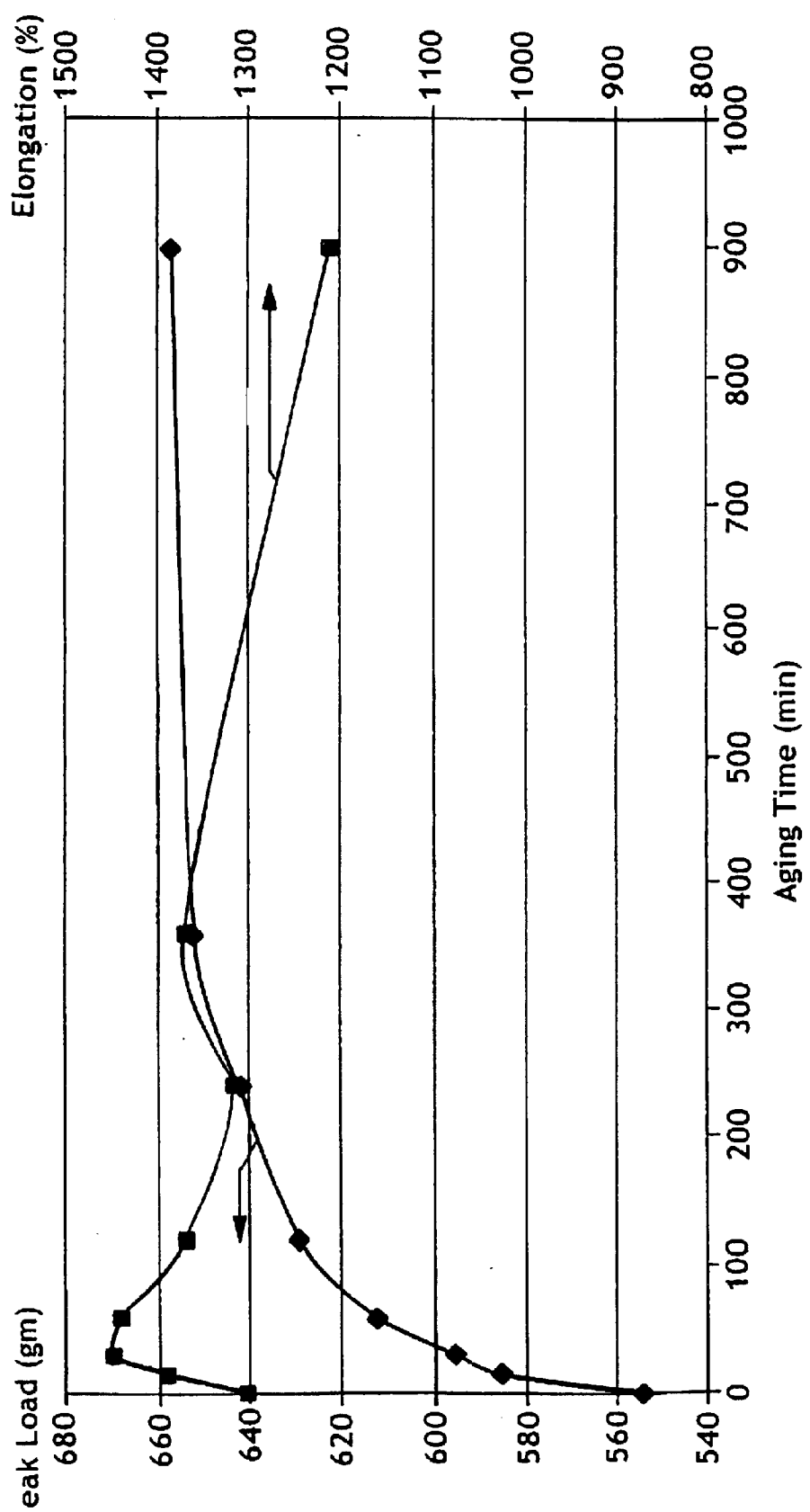
FIG. 5 shows a plot of peak-load value, in grams, and percent elongation as a function of time of exposure to a specified temperature.

Both the tensile strength and the elongation of a strand sample were determined using the equipment and procedure discussed in Example 1. Peak-load and elongation values plotted in FIG. 5 reflect the average of 5–10 replicates. This testing process was repeated at selected times of exposure to the specified temperature to give the plot depicted in FIG. 5. The data shows that the peak-load value this elastic strand material increased from about 550 grams to about 640 grams, an increase of about 15%, after exposure to a temperature of 100° C. for four hours.

Example 8

Bobbins of GLOSPAN 1060 were placed in a forced-air oven, model number OV-490A-2, made by Blue M. The oven was preheated to a temperature of 100° C. prior to bobbins of strand being placed in the oven. The bobbins of GLOSPAN 1060 had plastic cores with a 3-inch radius and a 10-inch length. The GLOSPAN 1060 elastic strand was wound around each core such that the strand material extended radially outwardly from the outer surface of the plastic core approximately 3 inches.

Both the tensile strength and the elongation of strand samples were determined using the equipment and procedure discussed in Example 1. For the heat-treated bobbins of elastic strand, some samples were obtained from the surface of the bobbin, some samples were obtained from the middle layer (i.e., approximately 1.5 inches from the outer surface of the plastic core), and some samples were obtained from a location next to the outer surface of the plastic core. Peak-load and elongation values in the table below reflect the average of 5–10 replicates. This testing process was repeated at 2 and 4 hours of exposure to a temperature of 100° C. to give Table 1 below.

TABLE 1

| Time of Exposure to 100° C. | Bobbin Location of Sample | | | | | |
|---|---|---|---|---|---|---|
| | Surface | | Middle | | Core | |
| Elonga-tion [hr] | Peak-load value [g] | Elonga-tion [%] | Peak-load value [g] | Elonga-tion [%] | Peak-load value [g] | Elonga-tion [%] |
| 2.0 | 590 | 1262 | 597 | 1415 | 588 | 1377 |
| 4.0 | 592 | 1222 | 614 | 1436 | 608 | 1352 |

The initial peak-load value and elongation of the GLOSPAN 1060 before heat treatment were about 550 grams and 1300%, respectively. The above data demonstrates that strength is improved by heat treatment of bobbins, but the increase in strength is less than the increase in strength found in Example 7 for individual strand samples. Furthermore, the data show that the elastic strand appears to have experienced a relatively uniform increase in strength throughout the bobbin.

Example 9

A bobbin of LYCRA 1040, an elastic strand comprising a polyether-b-polyurethane block copolymer, was obtained from Dupont Corp., a business having offices in Wilmington, Del. Samples of the strand were placed in a forced-air oven, model number OV490A-2, made by Blue M, a business having offices at Blum Island, Ill. The oven was preheated to a temperature of 100° C. prior to samples of the strand being placed in the oven. At selected times of exposure to these conditions, samples of the strand were withdrawn from the oven and taken to a testing room. Generally about 15 to 30 minutes elapsed between the time a sample was withdrawn from the controlled environment and the time the sample was tested.

Both the tensile strength and the elongation of a strand sample were determined using the equipment and procedure discussed in Example 1. The peak-load value of a sample that was not heat treated was 715 grams, and the corresponding elongation was 978%. The peak-load value of LYCRA1040 after being heated at a temperature of 100° C. for 1 hour was 757 grams, about a 5% increase, and the elongation was 930%. The peak-load value of LYCRA1040 after being heated at a temperature of 100° C. for 24 hour was 812 grams, about a 13% increase, and the elongation was 1126%.

Example 10

A bobbin of GLOSPAN 840 (Globe), an elastic strand comprising a polyester-b-polyurethane block copolymer, was obtained from Globe Manufacturing Company. The elastic strand had been coated with a silicone-based lubricant. Samples of the strand were placed in a controlled environment, with the temperature controlled to a value of 100° F. and the relative humidity controlled to a value of 80%. At selected times of exposure to these conditions, samples of the strand were withdrawn from the controlled environment and taken to a testing room. Generally about 15 to 30 minutes elapsed between the time the sample was withdrawn from the controlled environment and the time the sample was tested.

Both the tensile strength and the elongation of a strand sample were determined using a Sintech tensile tester, available from MTS System Corporation of Eden Prairie, Minn. The opposing holders on the tensile tester consisted of cylindrical rods 60, as shown in FIGS. 4 and 4.A. The gauge length was set at 1.5 inches by moving the holders such that the central axes 62 of the rods were 1.5 inches apart. One end of a length of strand was then wrapped twice around one cylinder. The other end was then taken and wrapped twice around the other cylinder. The tester was then activated so that the opposing holders moved in opposite directions at a crosshead speed of 20±0.4 inches min$^{-1}$. The strand was pulled apart at this speed until the strand broke. The peak-load value, in grams, and percent elongation, which reflects the change in length per unit length, were recorded at the point where the strand broke. This testing process was repeated at selected times of exposure to the specified conditions of relative humidity and temperature to give the tensile strength (i.e., peak-load values) as follows (each value reflects the average of 5–10 replicates: before being exposed to a temperature of 100° F. and a relative humidity of 80% the peak-load value of the strand was about 375 grams (with a percent elongation of about 1080%); after exposure to these specified conditions for approximately 5 days, the peak-load value had decreased to about 345 grams (with a percent elongation of about 1175%); after exposure to these specified conditions for approximately 18 days, the peak-load value had decreased to about 250 grams (with a percent elongation of about 1200%); after exposure to these specified conditions for approximately 30 days, the peak-load value had decreased to about 245 grams (with a percent elongation of about 1145%); and after exposure to these specified conditions for approximately 65 days, the peak-load value had decreased to about 150 grams (with a percent elongation of about 870%).

Example 11

Samples from the same bobbin of GLOSPAN 840 discussed in Example 1 were placed in a heated environment, with the temperature at 120° F. and the relative humidity at 20%. Using the same procedure described in Example 1, samples of the strand were tested at selected times of exposure to these conditions to give the following (each value reflects the average of 5-10 replicates: before being exposed to a temperature of 120° F. and a relative humidity of 20% the peak-load value of the strand was about 375 grams (with a percent elongation of about 1080%); after exposure to these specified conditions for approximately 50 hours, the peak-load value was about 400 grams (with a percent elongation of about 1125%); after exposure to these specified conditions for approximately 180 hours, the peak-load value was about 455 grams (with a percent elongation of about 1250%); and after exposure to these specified conditions for approximately 500 hours, the peak-load value was about 410 grams (with a percent elongation of about 1275%).

Example 12

Samples from a bobbin of LYCRA 940 from Dupont Corporation of Wilmington, Del. were placed in an environment with relative humidity controlled to a value of 80% and temperature controlled to a value of 100° F. After 2 months' exposure to these conditions, samples of LYCRA 940 exhibited a peak-load value 10% lower than the peak-load value of LYCRA 940 that had not been exposed to these conditions.

Although the present invention has been described in considerable detail with reference to certain versions, other versions are possible. The spirit and scope of the appended claims should not be limited to the description of specific versions contained herein.

What is claimed is:

1. Elastic strand treated by a method comprising the steps of:
    providing an elastic strand, the elastic strand having been made by steps comprising extruding or spinning the strand; and
    heating the elastic strand such that the strand's peak-load value increases by at least about 10%.

2. The elastic strand of claim 1 wherein the elastic strand comprises polyester, polyurethane, polyether, polyamide, polyacrylate, polyester-b-polyurethane block co-polymer, a polyether-b-polyurethane block co-polymer, or a polyether-b-polyamide block co-polymer; and wherein the elastic strand is heated by infrared radiation, microwave radiation, convective heat, conductive heat, or some combination thereof.

3. The elastic strand of claim 1 wherein the method of treating the strand further comprises the step of regulating the elastic strand's exposure to water vapor before, during, or after heating such that the specific humidity around the strand does not exceed about 0.01 pounds-mass of water vapor p r pound-mass of dry air during production of the strand, storage of the strand at the geographic site where the elastic strand is made, shipping of the strand between the geographic site where the elastic strand is made and the geographic site where the elastic strand is to be used as a raw material, storage of the elastic strand at the geographic site where the elastic strand is to be used as a raw material, use of the elastic strand as a raw material, or some combination thereof.

4. The elastic strand of claim 1 wherein the method of treating the strand further comprises the step of regulating the elastic strand's exposure to water vapor before or after heating, the method comprising the additional steps of:
    placing the strand in a container comprising a barrier material; and
    closing the container.

5. The elastic strand of claim 4 wherein the container comprising a barrier material is closed at a time $t_1$, time $t_1$ being after the time when the strand is first produced and before the time when the strand is shipped from the geographical site at which the strand is first produced to the geographical site at which the strand is used; and wherein the specific humidity around the strand does not exceed 0.017 pounds-mass of water vapor per pound-mass of dry air between time $t_1$ and time $t_2$, time $t_2$ being the time when the closed container comprising a barrier material is first opened.

6. The elastic strand of claim 5 wherein the barrier material comprises polyethylene, polypropylene, polyvinyl chloride, polyvinylidene chloride, polyester, polycarbonate, nylon, cellulose, or a combination thereof: and wherein closing the container comprising a barrier material comprises heat sealing the container, the barrier material, or both.

7. The elastic strand of claim 6 further comprising the step of placing desiccant material with the strand before heat sealing the container, the barrier material, or both.

8. A substrate composite comprising the elastic strand of claim 1.

9. A substrate composite comprising the elastic strand of claim 2.

10. A substrate composite comprising the elastic strand of claim 3.

11. A substrate composite comprising the elastic strand of claim 4.

12. A substrate composite comprising the elastic strand of claim 5.

13. A substrate composite comprising the elastic strand of claim 6.

14. A substrate composite comprising the elastic strand of claim 7.

15. A disposable absorbent product comprising the substrate composite of claim 8.

16. A disposable absorbent product comprising the substrate composite of claim 9.

17. A disposable absorbent product comprising the substrate composite of claim 10.

18. A disposable absorbent product comprising the substrate composite of claim 11.

19. A disposable absorbent product comprising the substrate composite of claim 12.

20. A disposable absorbent product comprising the substrate composite of claim 13.

* * * * *